(12) United States Patent
Nambu et al.

(10) Patent No.: US 7,732,050 B2
(45) Date of Patent: Jun. 8, 2010

(54) SILICONE-MODIFIED WATER-ABSORBING POLYMER PARTICLES AND METHOD FOR PRODUCING THE SAME

(75) Inventors: Hiromi Nambu, Wakayama (JP);
Tetsuji Kitoh, Wakayama (JP);
Yoshihiro Hasebe, Wakayama (JP)

(73) Assignee: Kao Corporation, Tokyo (JP)

( * ) Notice: Subject to any disclaimer, the term of this patent is extended or adjusted under 35 U.S.C. 154(b) by 1070 days.

(21) Appl. No.: 10/137,405

(22) Filed: May 3, 2002

(65) Prior Publication Data

US 2003/0065087 A1    Apr. 3, 2003

(30) Foreign Application Priority Data

May 16, 2001    (JP)    ............................. 2001-146733

(51) Int. Cl.
*B32B 1/00*    (2006.01)
(52) U.S. Cl. .................. 428/407; 428/403; 524/588
(58) Field of Classification Search ................ 428/403, 428/404, 405
See application file for complete search history.

(56) References Cited

U.S. PATENT DOCUMENTS

| | | | | |
|---|---|---|---|---|
| 5,091,443 A | * | 2/1992 | Karakelle et al. | ........... 424/665 |
| 5,668,078 A | | 9/1997 | Sumiya et al. | .............. 502/402 |
| 5,973,042 A | * | 10/1999 | Yoshinaga et al. | .......... 524/192 |

FOREIGN PATENT DOCUMENTS

| | | |
|---|---|---|
| AU | B-25757/95 | 1/1996 |
| EP | 0 620 260 | 10/1994 |
| JP | 60-81120 | 5/1985 |
| JP | A 4-339 810 | 11/1992 |
| JP | 9-13966 | 1/1997 |
| WO | WOA 95/33558 | 12/1995 |
| WO | WO 98/47951 | 10/1998 |

OTHER PUBLICATIONS

Patent Abstracts of Japan, JP 08-319218, Dec. 3, 1996.
Derwent Abstracts, AN 1997-399390. XP-002224818, JP 09-175939, Jul. 8, 1997.
Patent Abstracts of Japan, JP 05-070322, Mar. 23, 1993.
Derwent Abstracts, AN 1997-337115, XP-002224877, JP 09-136966, May 27, 1997.
Pending U.S. Appl. No. 10/053,658, filed Jan. 24, 2002.
U.S. Appl. No. 10/534,753, filed May 13, 2005, Nambu, et al.

* cited by examiner

*Primary Examiner*—Monique R Jackson
(74) *Attorney, Agent, or Firm*—Oblon, Spivak, McClelland, Maier & Neustadt, L.L.P.

(57) ABSTRACT

This invention provides water-absorbing polymer particles suitable particularly for cosmetics, wherein silicone can be stably present on the surface of a water-absorbing polymer even in various formulations thereby giving dry feeling in use even after water absorption. The silicone-modified water-absorbing polymer particles of this invention comprises water-absorbing polymer particles coated thereon via chemical bonding, with a silicone compound having at least one functional group.

15 Claims, 1 Drawing Sheet

SILICONE-MODIFIED WATER-ABSORBING POLYMER PARTICLES AND METHOD FOR PRODUCING THE SAME

TECHNICAL FIELD OF THE INVENTION

This invention relates to water-absorbing polymer particles coated thereon via chemical bonding, with a silicone compound having at least one kind of functional group and a process for producing the same and in particular to silicone-modified water-absorbing polymer particles useful in cosmetics, for example skin care products such as sweat regulators, hair care products, make-up products, etc.

PRIOR ART

The water-absorbing polymer is utilized as a sanitary material in sanitary items and diapers, as a water-retaining agent and soil conditioner in the field of agriculture, and artificial snow in an artificial skiing ground, a scrubbing agent in a cleansing cream etc. in various fields. In addition to these uses, JP-A No. 60-81120 discloses that self-crosslinked poly (sodium acrylate) is utilized as a sweat-absorbing sweat regulator in the field of cosmetics. However, this water-absorbing polymer is problematic in stickiness after absorption of sweat.

On one hand, there is known a method wherein the surface of a water-absorbing polymer is crosslinked via polyvalent metal ions or by an organic crosslinking agent, or rendered hydrophobic by hydrophobic materials such as nonvolatile hydrocarbons or calcium stearate powder, whereby the water-absorbing polymer after water absorption is prevented from becoming sticky or causing gel blocking (phenomenon of forming lumps).

For example, JP-A No. 9-13966 discloses a water-absorbing resin prepared by modifying a water-absorbing resin with a silicone type surfactant having an HLB of 7 to 18. In this method, however, there is a problem that the silicone type surfactant is adsorbed physically onto the surface of the water-absorbing resin, and owing to interaction with other components in cosmetic formulations, the surfactant cannot be stably present on the surface of the water-absorbing resin.

SUMMARY OF INVENTION

The problem of this invention is to provide water-absorbing polymer particles wherein silicone can stably be present on the surface of the water-absorbing polymer particles even in various formulations thereby giving dry feeling for use even after water absorption.

The present inventors found that if silicone is allowed to be present in an irreversible binding state on the surface of water-absorbing polymer particles, the resultant silicone-modified water-absorbing polymer particles have a high ability to absorb water without becoming sticky even after swollen with water absorbed, and the physical properties of the polymer particles can also be demonstrated in various formulations.

That is, this invention relates to silicone-modified water-absorbing polymer particles wherein the surfaces of water-absorbing polymer particles have been coated via chemical bonding with a silicone compound having at least one functional group and then the silicone-modified water-absorbing polymer particles of this invention are obtainable and produced by the step of polymerizing a hydrophilic vinyl monomer by reverse phase suspension polymerization in the reaction system in the presence of a silicone compound having at least one functional group, or by reacting a silicone compound having at least one functional group with the surface of water-absorbing polymer particles. Further, this invention relates to cosmetics comprising the silicone-modified water-absorbing polymer particles described above.

[Embodiment of the Invention]

The shape of the silicone-modified water-absorbing polymer particles of this invention is not particularly limited, and may be not only in the form of sphere, egg or lump, but also in the form of scale, plate, fiber, fine-powder agglomerate (granule) or in an amorphous state. Preferably, the silicone-modified water-absorbing polymer particles are in the form of sphere, egg or lump for easy availability, more preferably in the form of sphere for good feeling. These particles may be porous.

When the silicone-modified water-absorbing polymer particles of this invention are in the form of sphere, egg or lump, the average particle diameter thereof is preferably 0.1 μm to 500 μm, more preferably 0.5 μm to 250 μm, particularly preferably 1 μm to 150 μm and most preferably 1 to 50 μm so that the particles are not remarkable in cosmetics. The average particle diameter can be determined by analyzing sections of dried water-absorbing polymer particles under an optical microscope.

The amount of water absorbed into the silicone-modified water-absorbing polymer particles of this invention can be determined by a method of measuring the amount of absorbed water as described later. The amount of absorbed water is preferably 5 g/g to 500 g/g, more preferably 5 g/g to 100 g/g, particularly preferably 5 g/g to 50 g/g and most preferably 5 g/g to 20 g/g. The polymer particles in this range are preferable because they absorb water sufficiently and feel less sticky.

The silicone-modified water-absorbing polymer particles of this invention are water-absorbing polymer. particles wherein the surfaces of water-absorbing polymer particles have been coated via chemical bonding with a silicone compound having at least one kind of functional group, and the polymer particles have the silicone compound having at least one kind of functional group on the surfaces of the water-absorbing polymer particles via said functional group by chemical bonding, preferably covalent bonding and/or ionic bonding to a functional group present on the surfaces of the water-absorbing polymer particles. To confirm the presence of such chemical bonding, whether or not silicone is present on the water-absorbing polymer particles is examined after subjecting the silicon-modified polymer particles 3 times to the washing step of treating, with chloroform, the silicone-modified polymer particles (10% by weight relative to chloroform) for 2 hours under stirring (30 rpm, 50° C.) and then centrifuging the particles.

Figure 1:
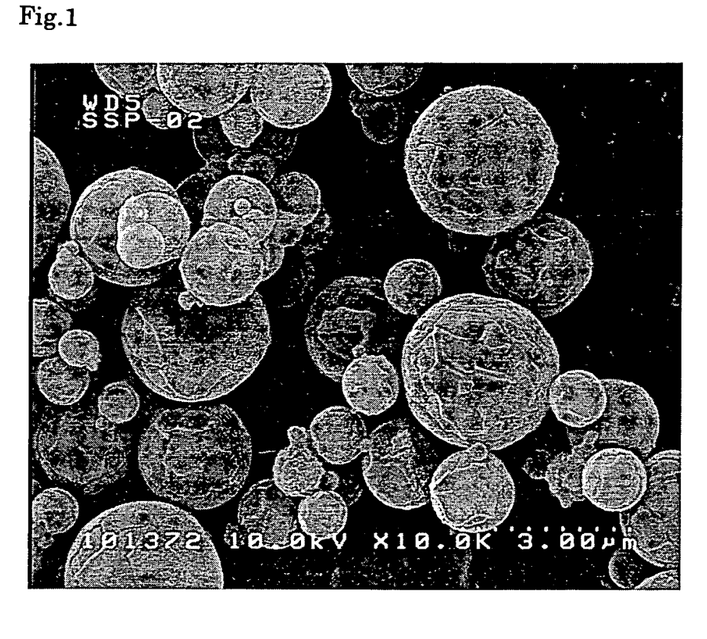
FIG. 1 is a photograph by SEM (scanning electron microscope) of the silicone-modified polymer particles obtained in Example 1.
Figure 2:
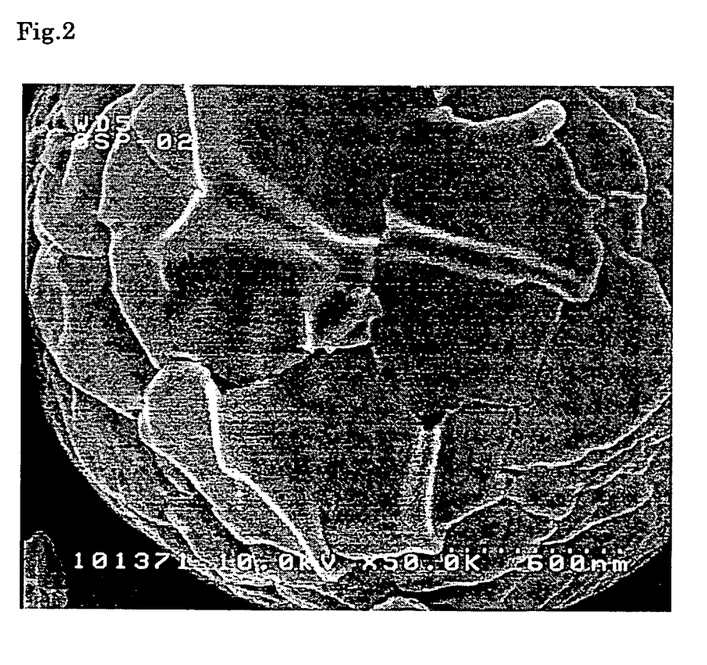
FIG. 2 is an enlarged photograph by SEM of the silicone-modified polymer particles in FIG. 1.

The term "coated" means that the surfaces of the water-absorbing polymer particles are coated at least partially to such an extent that the surfaces of the particles swollen with absorbed water are prevented from becoming sticky. A SEM photograph of the silicone-modified water-absorbing polymer particles of this invention in a dry state is shown in FIGS. 1 and 2.

With respect to the amount of the silicone having at least one kind of functional group on the water-absorbing polymer particles, the lower limit thereof is preferably at least 0.1 part by weight, more preferably at least 0.5 part by weight and particularly preferably at least 1 part by weight relative to 100 parts by weight of the water-absorbing polymer particles. The upper limit thereof is preferably at most 30 parts by weight, more preferably at most 10 parts by weight and particularly preferably at most 5 parts by weight. An amount of the silicone in this range is preferable because there is no particular sticky feeling after water absorption, and the rate of water absorption is not particularly inhibited.

The silicone-modified water-absorbing polymer particles of this invention are produced from the starting materials by the production method as described later.

[Water-absorbing Polymer Particles]

As the polymer used in the water-absorbing polymer particles of this invention, a natural polymer, a semi-synthetic polymer or a synthetic polymer can be used insofar as it is a polymer having the action of absorbing water. To attain water-retaining properties, it may be a polymer having a crosslinked structure, and such a polymer is a (co)polymer crosslinked by a crosslinking method described later or a (co)polymer having a crosslinkage via a hydrogen bond or hydrophobic bond, a crosslinkage derived from a partial crystalline structure or a crosslinkage derived from a helix structure etc. [(co)polymer means a polymer or copolymer.].

For example, the natural polymer and semi-synthetic polymer include starch, carrageenan, gelatin, agar, tragacanth gum, viscose, cellulose (for example, crystalline cellulose), methyl cellulose, ethyl cellulose, hydroxyethyl cellulose and carboxymethyl cellulose, or crosslinked products thereof, for example starch-(meth)acrylate graft copolymers (or its crosslinked products) [(meth)acrylate means acrylate, methacrylate or a mixture thereof.].

The synthetic polymer includes a crosslinked product of a (co)polymer of a hydrophilic monomer such as anionic monomers or salts thereof, nonionic hydrophilic group-containing monomers, amino group-containing monomers or acid-neutralized products thereof or quaternarized products thereof. In particular a hydrophlic vinyl monomer is preferable because it is easily manufactured. The hydrophilic property of the hydrophilic monomer means that the solubility in 100 g of water at 25° C. is preferably 6 wt. % or more, more preferably more than 20 wt. %.

Examples of monomers used in production of the synthetic polymer include anionic monomers such as (meth)acrylic acid, maleic acid, fumaric acid, crotonic acid, itaconic acid, 2-(meth)acryloyl ethane sulfonic acid, 2-(meth)acryloyl propane sulfonic acid, 2-(meth)acrylamide-2-methyl propane sulfonic acid, vinyl sulfonic acid and styrene sulfonic acid or salts thereof; nonionic hydrophilic group-containing monomers such as (meth)acrylamide, N-substituted (meth)acrylamide, 2-hydroxyethyl (meth)acrylate, 2-hydroxypropyl (meth)acrylate, methoxypolyethylene glycol (meth)acrylate, polyethylene glycol(meth)acrylate, N-vinyl pyrrolidone and N-vinyl acetamide; and amino-group containing monomers such as N,N-dimethylaminoethyl (meth)acrylate, N,N-dimethylaminopropyl (meth)acrylate and N,N-dimethylaminopropyl (meth)acrylamide or acid-neutralized product thereof, or quaternarized products thereof. The quaternizing agents which are advantageously used for producing the quaternary ammonium salts include an alkylhalide such as methyl chloride, ethyl chloride, methyl bromide and methyl iodide, and standard alkylating agents such as dimethyl sulfate, diethyl sulfate and di-n-propyl sulfate, for example. The acids which are advantageously used for producing the acid-neutralized compounds include hydrochloric acid, sulfuric acid, nitric acid, acetic acid, formic acid, maleic acid, fumaric acid, citric acid, tartaric acid, adipic acid, sulfamic acid, toluene sulfonic acid, lactic acid. Unless the hydrophilicity of the resultant polymer is extremely inhibited, the hydrophobic monomers such as acrylates, for example methyl (meth)acrylate, ethyl (meth)acrylate and butyl (meth) acrylate, vinyl acetate and vinyl propionate can also be simultaneously copolymerized in an amount of not higher than 50% by weight, more preferably 20 wt. % or less, of the total monomers.

The hydrophobic property means that the solubility in 100 g of water at 25° C. is preferably less than 6 wt. %, more preferably 3 wt. % or less. No lower limit is provided. It may be 0.01 wt. % or more.

As the monomer components used, one or more of those enumerated above can be selected, but crosslinked copolymers of α,β-unsaturated monocarboxylic acid monomers such as (meth)acrylic acid, maleic acid, fumaric acid, crotonic acid, itaconic acid or salts thereof are preferable because of the high water-absorbing ability and easy availability. In addition to the α,β-unsaturated carboxylic acid monomers, other monomers can also be copolymerized. To improve the water-absorbing ability, the amount of α,β-unsaturated carboxylic acid monomers is preferably at least 50% by weight, more preferably at least 70% by weight and particularly preferably at least 90% by weight of the total monomers.

The polymer is more preferably a partially crosslinked polymeric compound having a carboxyl group or a salt thereof, such as crosslinked poly(meth)acrylate, a crosslinked poly(vinyl alcohol/(meth)acrylate) copolymer, a starch-(meth)acrylate graft copolymer and a crosslinked polyvinyl alcohol-poly(maleic anhydride) graft copolymer, particularly preferably crosslinked poly(meth)acrylate or a crosslinked starch-(meth)acrylate graft copolymer, further preferably crosslinked poly(meth)acrylate for a higher water-absorbing ability, and most preferably crosslinked methacrylate for higher pKa and a higher deodorizing ability as described below. These water-absorbing polymers can be used alone or in combination thereof.

The "salt" includes e.g. alkali metal salts (sodium salt, potassium salt, lithium salt etc.), alkaline earth metal salts (calcium salt, magnesium salt, barium salt etc.) and ammonium salts (quaternary ammonium salt, quaternary alkyl ammonium salt etc.). Among these, the sodium salt is most inexpensive and preferable.

Here, the degree of neutralization of the water-absorbing polymer particles is preferably 0.01 to 100%, more preferably 1 to 99% and particularly preferably 40 to 95% based on the number of moles of the acid or base group in the water-absorbing polymer.

In this invention, the "degree of neutralization" refers to the ratio (on a molar basis) of the salt-forming group to the acid or base group in the water-absorbing polymer, that is, (number of moles of the salt-forming acid or base group)/(number of moles of the salt-formable free acid or base group plus the salt-forming acid or base group)×100 (%).

[Crosslinking Method and Crosslinking Agent]

The method of forming the crosslinked (co)polymers described above involves covalent crosslinking by (a) self-crosslinking during polymerization, (b) copolymerization with a multifunctional monomer, and (c) irradiation with radiation, or ionic crosslinking via (d) polyvalent metal ion. Among these, (b) is preferable from the viewpoint of easy production and stability of the crosslinked structure, and the multifunctional monomer includes a crosslinking vinyl monomer having at least 2 reactive unsaturated groups in the molecule and a compound having at least 2 functional groups other than unsaturated groups in the molecule.

As will be described in Production Method 1 below, crosslinking is conducted preferably during polymerization reaction by the method (a), (b) or (d) described above, but it is also preferable that after polymerization reaction, both the crosslinking agent and silicone-modified water-absorbing polymer particles are allowed to be present and the surface of the polymer particles is crosslinked by the method (b) or (d) is also preferable. It is also preferable that both the methods are conducted.

As will also be described in Production Method 2 below, the crosslinking method (b) or (d) described above is also preferably used when the water-absorbing polymer (or particles) is reacted with silicone having at least one kind of functional group.

In the method (b), the crosslinking vinyl monomer having at least 2 reactive unsaturated groups in the molecule includes (1) polyhydric alcohol (meth)acrylates such as ethylene glycol di(meth)acrylate, diethylene glycol di(meth)acrylate, polyethylene glycol di(meth)acrylate, propylene glycol di(meth)acrylate, dipropylene glycol di(meth)acrylate, polypropylene glycol di(meth)acrylate, 1,2-butylene glycol di(meth)acrylate, 1,3-butylene glycol di(meth)acrylate, neopentyl glycol di(meth)acrylate, glycerine di(meth)acrylate, glycerine tri(meth)acrylate, trimethylol propane tri(meth)acrylate, and pentaerythritol tetra(meth)acrylate; (2) acrylamide compounds such as N-methyl allyl acrylamide, N-vinyl acrylamide, N,N'-methylene bis(meth)acrylamide, and bisacrylamide acetate; (3) divinyl compounds such as divinyl benzene, divinyl ether, and divinyl ethylene urea; (4) polyallyl compounds such as diallyl phthalate, diallyl maleate, diallyl amine, triallyl amine, triallyl ammonium salt, pentaerythritol allyl ether, and sucroze [phonetic] allyl ether having at least 2 allyl ether units in the molecule; and (5) unsaturated alcohol (meth)acrylates such as vinyl (meth)acrylate, allyl (meth)acrylate, and 2-hydroxy-3-acryloyloxy propyl (meth)acrylate.

Among these crosslinking vinyl monomers having at least 2 reactive unsaturated groups in the molecule, ethylene glycol di(meth)acrylate, polyethylene glycol di(meth)acrylate, divinyl benzene, pentaerythritol triallyl ether, pentaerythritol tetraallyl ether, and methylene bisacrylamide are preferable.

The compound having at least 2 functional groups other than unsaturated groups in the molecule includes (6) polyhydric alcohols such as ethylene glycol, diethylene glycol, triethylene glycol, polyethylene glycol, glycerine, polyglycerine, propylene glycol, 1,4-butanediol, 1,5-pentanediol, 1,6-hexanediol, neopentyl alcohol, diethanol amine, tridiethanol amine, polypropylene glycol, polyvinyl alcohol, pentaerythritol, sorbitol, sorbitan, glucose, mannitol, mannitan, sucrose and glucose; (7) polyglycidyl ethers such as ethylene glycol diglycidyl ether, polyethylene glycol diglycidyl ether, glycerine triglycidyl ether and polyglycerol polyglycidyl ether; (8) haloepoxy compounds such as epichlorohydrin and α-methyl chlorohydrin; (9) polyaldehydes such as glutaraldehyde and glyoxal; (10) polyamine compounds such as ethylene diamine and polyethylene imine; and (11) polyvalent carboxylic acids such as oxalic acid, malonic acid, succinic acid, fumaric acid, maleic acid and adipic acid.

Among these compounds having at least 2 functional groups other than unsaturated groups in the molecule, ethylene glycol diglycidyl ether and polyethylene glycol diglycidyl ether are preferably used.

In the method (d), the polyvalent metal salt includes (12) aluminum salts, magnesium salts and calcium salts, specifically hydroxides, halides, carbonates and oxides with metals in the groups 2A, 3B and 8 in the long form of the periodic table, such as calcium hydroxide, calcium chloride, calcium carbonate, calcium oxide, magnesium borax chloride, magnesium oxide, aluminum chloride, zinc chloride and nickel chloride, borates such as borax, and metal alkoxides such as aluminum isopropylate. One or more of these metals salts can be used in consideration of reactivity.

The amount of the crosslinking agent added is varied depending on the type of the crosslinking agent and the crosslinking method, but is preferably 0.001 to 20 parts by weight, more preferably 0.01 to 10 parts by weight, particularly preferably 0.01 to 5 parts by weight relative to 100 parts by weight of the total monomers in the reaction system. When the amount of the crosslinking agent is at least 0.001 part by weight, the amount of water absorbed can be maintained due to a low content of water-soluble components in the resulting water-absorbing polymer, while when its amount is at most 20 parts by weight, the density of crosslinkages is suitable and the amount of water absorbed into the resultant water-absorbing polymer is sufficient.

[Silicone Compound having at Least One Kind of Functional Group]

The silicone compound having at least one kind of functional group used in this invention is a silicone compound having at least 2 or more silicon atoms, having at least one functional group capable of chemical bonding, preferably covalent bonding and/or ionic bonding, to the surface of water-absorbing polymer particles.

To prevent gel blocking among polymer particles or sticky feeling during use, the silicone compound is preferably hydrophobic. In particular, when the silicone compound is the one having plural kinds of functional groups, which has a functional group not contributing to the reaction, the silicone compound is preferably hydrophobic.

The hydrophobic compound having at least one kind of functional group refers to the one whose solubility in 100 g water at 25° C. is at most 10% by weight, preferably at most 1% by weight, more preferably at most 0.5% by weight and particularly preferably at most 0.1% by weight. The lower limit of the solubility is not particularly present, but may be at least 0.0001% by weight.

The weight average molecular weight of the silicone having at least one kind of functional group used in this invention is preferably 1000 to 500,000, more preferably 3000 to 200,000 and particularly preferably 10,000 to 200,000. Measurement of this weight average molecular weight is conducted by gel permeation chromatography (GPC) using polystyrene as standard and chloroform as eluent.

The functional group is preferably at least one kind of functional group selected from the group consisting of an amino group, ammonium group, hydroxy group, a carboxy group, an epoxy group, a hydrolysable alkoxy group and radical-polymerizable unsaturated group, more preferably at least one kind of functional group selected from the group consisting of an amino group, ammonium group, carboxy group, epoxy group and radical reactive unsaturated group, and particularly preferably an amino group and/or ammonium group. These groups may be located at a side chain, one end and/or both ends of siloxane, or may be a mixture thereof. Examples of the silicone compound having at least one kind of functional group used in this invention are shown below.

1) Silicone Compound having an Amino Group and/or Ammonium Group (Referred to Hereinafter as Amino-modified Silicone)

The amino-modified silicone compound is preferably the one having polymerizable units represented by the general formula (1) below. In the general formula (1), $R^1$ groups independently represent a hydrogen atom or a $C_{1-6}$ hydrocarbon group, for example an alkyl group or phenyl group, preferably a methyl group or ethyl group, more preferably a methyl group.

wherein $R^1$ represents a hydrogen atom or a $C_{1-6}$ hydrocarbon group; $R^2$ represents $R^1$ or X whereupon X is a reactive functional group represented by —$R^3$—Z ($R^3$ represents a direct bond or a $C_{1-20}$ divalent hydrocarbon group, and Z represents a primary to tertiary amino group-containing group or a quaternary ammonium group-containing group); and a is an integer of 2 or more, and b is an integer of 1 or more.

In the general formula (1), $R^3$ is preferably a $C_{1-6}$ linear or branched alkylene group, and includes a methylene group, ethylene group, trimethylene group, propylene group, tetramethylene group etc., more preferably a trimethylene group or propylene group.

In the general formula (1), a and b each represent the number of polymerizing repeating units. Preferably, a is a number of 2 to 1000, and b is a number of 1 to 50.

In the general formula (1), Z is preferably an amino group- or ammonium group-containing group represented by the general formula (2) or (3) below.

wherein $R^4$ represents —OCH$_2$CH$_2$—, —OCHCH$_2$—,
                                                   |
                                                  CH$_3$
—OCH$_2$CHCH$_2$—  or  —OCH$_2$CH—,
          |                              |
         OH                         CH$_2$OH

$R^5$ and $R^6$ each are the same as or different from one another and represent a hydrogen atom or a monovalent hydrocarbon group, d and e each are the same as or different from one another and represent an integer of 0 to 6, and T represents a halogen ion or an organic anion.

In the general formula (1), the group X is preferably —(CH$_2$)$_3$—NH$_2$, —(CH$_2$)$_3$—N(CH$_3$)$_2$—, —(CH$_2$)$_3$—NH—(CH$_2$)$_2$—NH$_2$, —(CH$_2$)$_3$—NH—(CH$_2$)$_2$—N(CH$_3$)$_2$, or —(CH$_2$)$_3$—N$^+$(CH$_3$)$_3$—Cl$^-$, more preferably —(CH$_2$)$_3$—NH—(CH$_2$)$_2$—NH$_2$. Examples of T$^-$ in the general formula (3) include halogen ions such as chlorine, iodine, bromine etc. and organic anions such as methosulfate, ethosulfate, methophosphate, ethophosphate etc.

The weight average molecular weight of the amino-modified silicone is preferably 3000 to 200,000, by GPC as mentioned above, and for easy reaction with anionic functional groups of the water-absorbing polymer and for hydrophobicity of silicone, the amine equivalent thereof is preferably 250 to 10000 (g/mol), more preferably 1000 to 5000(g/mol). The amine equivalent can be measured in a solvent such as chloroform, ethanol by titration with hydrochloric acid.

2) Silicone Compound having a Carboxy Group (Referred to Hereinafter as Carboxy-modified Silicone)

The carboxy-modified silicone compound is preferably either a compound having a silicon atom and carboxy group bound via a saturated hydrocarbon, or an organopolysiloxane compound having a carboxyl group and/or a salt thereof bound to a silicon atom via a structure shown in the general formulae (4) and/or (5), which is known in JP-A 2002-114849:

wherein $R^7$, $R^8$, $R^9$ and $R^{10}$ are the same or different and each represent a $C_{2-22}$ linear or branched alkylene group or alkenylene group or an arylene group, which may have a substituent group containing a heteroatom; X represents an —O— or —NH— group; and M represents a hydrogen atom, a metal, ammonium, $C_{1-22}$ alkyl or alkenyl ammonium, $C_{1-22}$ alkyl or alkenyl-substituted pyridinium, $C_{1-22}$ alkanol ammonium, or a basic amino acid.

Further, an amphoteric ionomer siloxane having two functional groups (carboxyl group and ammonium group) described in JP-A No. 6-1711 can also be preferably used.

The weight average molecular weight of the carboxy-modified silicone compound is preferably 3000 to 200,000 by GPC mentioned above. For easy reaction with cationic functional groups of the water-absorbing polymer and for hydrophobicity of silicone, the carboxy equivalent thereof is preferably 250 to 10000 (g/mol), more preferably 1000 to 5000 (g/mol). The carboxy equivalent can be measured in a solvent such as chloroform, ethanol by titration with sodium hydroxide.

3) Silicone Compound having an Epoxy Group (Referred to Hereinafter as Epoxy-modified Silicone)

The epoxy-modified silicone compound is preferably a silicone compound containing an epoxy group at one and/or both ends represented by the general formula (6):

wherein $R^{11}$ groups are the same or different and each represent a monovalent hydrocarbon group; $R^{12}$ represents an epoxy-containing group or a monovalent hydrocarbon group; A represents an epoxy-containing group; and n is an integer of 1 to 10000.

The monovalent hydrocarbon group represented by $R^{11}$ includes an alkyl group such as methyl group and ethyl group, a cycloalkyl group such as cyclohexyl group, an aryl group such as phenyl group, and a fluorine atom-substituted alkyl group such as trifluoropropyl group. All $R^{11}$ groups may be the same as or different from one another and are desirably methyl groups.

In the general formula (6), the epoxy-containing group represented by A is not particularly limited, but specifically includes the groups shown in the general formulae (7) to (9):

(7)

(8)

(9)

wherein a and b are an integer of 1 or more; c is an integer of one or more; AO is the same as or different from one another and ethylenoxy group or propyleneoxy group.

In the general formula (6), when $R^{12}$ represents the same group as in $R^{11}$, the compound is silicone containing an epoxy group at one end, while $R^{12}$ represents the same group as in A, the compound is silicone containing an epoxy group at both ends.

The epoxy-modified silicone is preferably silicone containing an epoxy group at one end, that is, silicone wherein $R^{12}$ is the same group as in $R^{11}$, wherein the hydrocarbon group is preferably an alkyl group such as methyl group and ethyl group, a cycloalkyl group such as cyclohexyl group, an aryl group such as phenyl group and a fluorine atom-substituted alkyl group such as trifluoropropyl group, more preferably a methyl group.

In the general formula (6), n is preferably 1 to 500, more preferably 5 to 100 and particularly preferably 10 to 50.

4) Silicone Compound having a Hydroxy Group

The silicone compound having a hydroxyl group includes the branched silicone of the general formula (10), the both-terminal type silicone of the general formula (11), and the one-terminal type silicone of the general formula (12). Then it further includes those having the formula (6) in which, however, the epoxy group having the formula (7), (8) or (9) is hydrolyzed and an alkylglyceryl ether-modified silicone disclosed in JP-A 5-112424.

The numbers represented by l, m and n respectively in the general formulae (10) to (12) may be preferably an arbitrary combination such that the HLB of the silicone having a hydroxy group is less than 7. More preferably, the HLB is 6 or less. The HLB can be determined by dividing the weight fraction of the polyoxyalkylene group by 5.

It is preferable that $R^{13}$ is methyl and $R^{14}$ is trimethylene.

(10)

(11)

(12)

wherein AO groups may be the same as or different from each other and represent an ethyleneoxy group or propyleneoxy group; $R^{13}$ is an alkyl having 1 to 4 carbon atoms; $R^{14}$ is the same as or different from each other and an alkylene having 1 o 8 carbon atoms; l is an integer of 1 or more and m and n are an integer of zero or more.

5) Silicone Compound having a Radical Polymerizable Unsaturated Group

The silicone compound having a radical polymerizable unsaturated group includes e.g. those compounds represented by the general formula (13):

(13)

wherein A is a group represented by $CH_2=C(R^{13})COO-$, $CH_2=C(R^{13})CONR^{14}-$ or $CH_2=CH-C_6H_4-$ whereupon $R^{13}$ is H or $CH_3-$, $R^{14}$ is H or $C_yH_{2y+1}-$ (Y=an integer of 1 to 4); B is a group represented by $-(CH_2O)_m-C_nH_{2n}-$ (m=0 or 1, n=an integer of 1 to 10); E is a group represented by $C_pH_{2p+1}-$ (p=an integer of 1 to 4); and a is an integer of 3 to 1500.

Among the compounds of the general formula (13), those compounds represented by the general formula (14) are particularly preferable in order to achieve the object of this invention.

(14)

wherein $R^{13}$, B and a have the same meanings as defined in the general formula (13) above, and $R^{15}$ represents a $C_{1-4}$ alkyl group.

The silicone compound having a radical polymerizable unsaturated group can be synthesized for example by a method of utilizing chain transfer by radical polymerization or a method of anion living polymerization.

The number average molecular weight (Mn) of the silicone compound having a radical polymerizable unsaturated group used in this invention is preferably 500 to 100,000, more preferably 1,000 to 50,000 by GPC as mentioned above, from the viewpoint of the dispersion stability of the formed polymer particles and operativeness for production of the polymer particles.

[Method of Producing Silicone-modified Water-absorbing Polymer Particles]

The method of producing the silicone-modified water-absorbing polymer particles according to this invention includes Production Method 1 or 2 described below. Production Method 1. Method of polymerizing the hydrophilic monomer in the presence of a silicone compound having at least one functional group In this method, the silicone having at least one functional group is added to the reaction system before and/or during polymerization of the hydrophilic monomer.

When a polymer of hydrophilic vinyl monomers is used as the water-absorbing polymer, the hydrophilic vinyl monomer may be polymerized by any method, but a method of polymerizing an aqueous solution of the hydrophilic vinyl monomer (preferably at a concentration of 1 to 70% by weight) is preferable, and various methods such as aqueous solution polymerization, reverse phase suspension polymerization and pearl polymerization can be used. In particular, aqueous solution polymerization or reverse phase suspension polymerization is preferable in respect of operativeness for polymerization and the water-absorbing ability of the resultant water-absorbing polymer, and reverse phase suspension polymerization is particularly preferable in respect of a higher water-absorbing ability of the water-absorbing polymer. The temperature for polymerization of the hydrophilic vinyl monomer is preferably 20 to 120° C. and the polymerization time is preferably 20 to 180 minutes.

As the initiator, a water-soluble radical polymerization initiator, for example a peroxide, hydroperoxide or an azo compound is known in a known amount. These polymerization initiators can be used as a mixture thereof, or can be used as redox type polymerization initiators by adding chromium ion, sulfite, hydroxylamine, hydrazine etc. thereto. If necessary, an oil-soluble radical polymerization initiator, for example a peroxide type initiator such as benzoyl peroxide or lauroyl peroxide, or an azo type initiator such as azobis(isobutyronitrile) can also be used.

The amount of the water-soluble polymerization initiator is preferably 0.03 to 5 wt. %, more preferably 0.1 to 2 wt. %, per the hydrophilic vinyl monomer.

A dispersant may be used to disperse the hydrophilic vinyl monomer stably in the oil phase(solvent). The above shown silicone compound having at least one functional group may be used as the dispersant. It may be combined with another dispersant. The dispersant of the silicone compound preferably has at least one functional group selected from amino group, ammonium group, hydroxy group and carboxy group.

The other dispersant may be an anionic, cationic, nonionic or amphoteric surfactant or a natural, semi-synthetic or synthetic polymer. For example, it includes an anionic surfactant such as sodium polyoxyethylene dodecyl ether sulfate and sodium dodecylether sulfate, a cationic or amphoteric surfactant such as trimethylstearylammonium chloride and carboxymethyldimethylcetyl ammonium, a saccharose fatty ester such as saccharose monostearate and saccharose dilaurate, a sorbitan ester such as sorbitan monostearate, a nonionic surfactant such as polyoxyalkylene adducts to sorbitan esters such as polyoxyethylenesorbitan monostearate, a natural or semi-synthetic polymer such as cellulose derivatives such as starch or derivatives thereof, cellulose ethers such as ethyl cellulose and cellulose esters such as cellulose acetate and a synthetic polymer such as polyvinyl alcohol or derivatives thereof, maleic group-having polybutadiene and a quaternary salt of styrene-dimethylaminoethyl methacrylate.

The dispersant may be present in an amount of 0.5 to 30 mass %, more preferably 1-10 mass %, in particular 1-7 mass %, per 100 mass % of the total vinyl monomer constituting the water-absorbing polymer particles.

The solvent used in reverse phase suspension polymerization is preferably a hydrocarbon type solvent or silicone type solvent or a mixture thereof. Examples of the hydrocarbon type solvent include aliphatic hydrocarbons such as hexane, heptane, dodecane, cyclohexane, methyl cyclohexane, isooctane and hydrogenated triisobutylene and aromatic hydrocarbons such as benzene, toluene, xylene and ethyl benzene, and examples of the silicone type solvent include octamethyl cyclotetrasiloxane, decamethyl cyclopentasiloxane, hexamethyl disiloxane and octamethyl trisiloxane. Among these solvents, hexane and cyclohexane are particularly preferable.

The method of producing silicone-modified water-absorbing polymer particles is preferably a method of polymerizing a hydrophilic vinyl monomer such as $\alpha,\beta$-unsaturated carboxylic acid monomer and/or a salt thereof by water-in-oil reverse phase suspension polymerization wherein before or during polymerization, the silicone having at least one kind of functional group is allowed to be present in the reaction system by adding it simultaneously with, or separately from, a crosslinking agent. The only surface of particle may be cross-linked by adding a cross-linking agent later and reacting under preferably 40 to 150° C. The "during polymerization" encompasses a period extending, after the reaction is substantially finished, to a stage before removal of water or solvent by e.g. distillation from the reaction system or before cooling.

It is preferable to polymerize a hydrophlic vinyl monomer and a crosslinking agent in the presence of a silicone having at least one functional group by reverse dispersion polymerization.

The silicone having at least one kind of functional group is hydrophobic, and by water-in-oil reverse phase suspension polymerization, this silicone is solubilized or uniformly dispersed in the oil phase, to occur in a larger amount on the surface of the water-absorbing polymer particles than in the inside thereof.

The silicone having at least one kind of functional group can be added directly or as a solution in which the silicone has been solubilized or dispersed by emulsification in an organic solvent, a surfactant etc. The crosslinking agent may be previously coexistent with the vinyl monomer or may be added during polymerization.

As the initiator, a peroxide such as benzoyl peroxide, potassium persulfate or sodium persulfate may be used for self-crosslinking.

In the reaction system, the silicone having at least one kind of functional group is allowed to be present in an amount of preferably 0.5 to 30 parts by weight, more preferably 1 to 10 parts by weight and particularly preferably 1 to 7 parts by weight relative to 100 parts by weight of the total hydrophilic vinyl monomers, whereby a sufficient amount of silicone can be present on the surface of the silicone-modified particles.

The amount of the crosslinking agent in the reaction system is as described above. Production Method 2. Method of allowing a previously obtained water-absorbing polymer particles such as a water-absorbing polymer particles after polymerization or a natural polymer to react with the silicone having at least one kind of functional group.

The method of producing silicone-modified water-absorbing polymer particles is preferably a method wherein a polymer of the hydrophilic vinyl monomer after polymerization or a previously prepared water-absorbing polymer particles (for example, a natural polymer) and the silicone having at least one functional group are allowed to be-present together and heated in the presence of water to which a crosslinking agent and/or a radical polymerization initiator is added if necessary. By the presence of water, functional groups in the water-absorbing polymer particles are dissociated to react readly with functional groups in the silicone. The amount of water in the reaction system is preferably 1 to 200 parts by weight, more preferably 10 to 100 parts by weight, relative to 100 parts by weight of the water-absorbing polymer (particles) After the reaction, the water is removed, for example, by distillation.

When the silicone compound having a radically polymerizable unsaturated group is used, the above shown oil-soluble radical polymerization initiator is preferably allowed to be coexistent.

The silicone having at least one kind of functional group can be added directly or as a solution wherein the silicone has been solubilized or dispersed by emulsification in an organic solvent, a surfactant or a dispersant, or in the form of a spray depending on the case. The dispersant includes ethyl cellulose, sugar ester or sorbitan ester. Heating for facilitating surface treatment is preferably in the range of 40 to 150° C.

The silicone having at least one kind of functional group may be mixed with the water-absorbing polymer before or after disruption of the polymer, but it is more preferable that the water-absorbing polymer is disrupted to form water-absorbing polymer particles whose water content is regulated in a suitable range by drying if necessary, and the water-absorbing polymer particles are mixed in e.g. a kneader with the silicone having at least one kind of functional group.

In Production Method 2, the amount of the silicone having at least one kind of functional group is preferably 0.5 to 30 parts by weight, more preferably 1 to 10 parts by weight and particularly preferably 1 to 7 parts by weight relative to 100 parts by weight of the water-absorbing polymer (particles). When a crosslinking agent is used, the crosslinking agent is allowed to be present in an amount of preferably 0.01 to 10 parts by weight, more preferably 0.01 to 5 parts by weight and particularly preferably 0.01 to 3 parts by weight relative to 100 parts by weight of the water-absorbing polymer (particles).

The organic solvent in which the silicone is solubilized or dispersed by emulsification in Production Methods 1 and 2 is not particularly limited, but an organic solvent having a boiling temperature in the range of 30 to 200° C. is preferable from the viewpoint of safety and operativeness. As a polar solvent, methanol, ethanol, isopropanol, chloroform, toluene etc. can be mentioned. As a non-polar solvent, aliphatic hydrocarbons and alicyclic hydrocarbons are preferable, and for example n-hexane, cyclohexane, ligroin etc. can be mentioned.

In the production method 1, the functional group of the silicone compound is preferably amino group, ammonium group, hydroxy group or carboxy group. In the production method 2, the functional group of the silicone compound is preferably amino group, ammonium group, hydroxy group, carboxy group, epoxy group, a hydrolysable alkoxy group or a radically polymerizable unsaturated group.

The reaction of the water-absorbing polymer particles with the silicone having at least one kind of functional group in Production Methods 1 and 2 is varied depending on the type of the functional group, and the reaction described below is preferable.

When a crosslinking agent is used, a binding reaction with the crosslinking agent as a linking group is also preferable.

For example, the functional groups of the water-absorbing polymer particles include a carboxyl group, sulfonate group, amino group, hydroxy group and ammonium group.

When the silicon having at least one kind of functional group is an amino-modified silicone compound, the water-absorbing polymer particles are preferably anionic polymers, more preferably polymers of $\alpha,\beta$-unsaturated carboxylic acid monomers and/or salts thereof. This is because by a chemical bonding of an amino group and/or ammonium group in the silicone having at least one kind of functional group with a carboxy group of the water-absorbing polymer particles, the polymer particles can have the silicone having at least one kind of functional group. Further, when polyglycidyl ether is used as the crosslinking agent, the polymer particles after reaction of an epoxy group in polyglycidyl ether with an amino group and/or ammonium group in the silicone can have the silicone having at lease one kind of functional group, via the crosslinking agent as a linking group.

When the silicone having at least one kind of functional group is a carboxy-modified silicone compound, the water-absorbing polymer particles are preferably polymers of amino group-containing unsaturated monomers or quaternarized monomers thereof, or polymers of $\alpha,\beta$-unsaturated carboxylic acid monomers and/or salts thereof. When the water-absorbing polymer particles are polymers of amino group-containing unsaturated monomers or quaternarized monomers thereof, the water-absorbing polymer particles can, directly via covalent or ionic bonding, have the silicone having at least one kind of functional group. When the water-absorbing polymer particles are polymers of $\alpha,\beta$-unsaturated carboxylic acid monomers and/or salts thereof, e.g. a polyvalent metal salt is used as the crosslinking agent, whereby the polymer particles can, via ionic bonding with the crosslinking agent as a linking group, have the silicone having at least one kind of functional group When the silicone having at least one kind of functional group is a silicone compound having a functional group selected from a hydroxyl group and epoxy group, the silicone compound is reacted with polymers of a, D unsaturated carboxylic acid monomers and/or salts thereof, whereby the polymer particles can, via chemical bonding, have the silicone having at least one kind of functional group.

The silicone-modified water-absorbing polymer particles of this invention produced from the starting materials by the production methods as described above is incorporated preferably into cosmetics to give its characteristics to the cosmetics as described below.

[Cosmetics]

The content of the silicone-modified water-absorbing polymer particles of this invention in cosmetics can be suitably selected depending on the object of cosmetics, and is not particularly limited, but the content is preferably 1 to 50% by weight, particularly preferably 1 to 30% by weight. When the amount of the polymer particles incorporated is at least 1% by weight, the feel of the cosmetics can be sufficiently improved.

The cosmetics of this invention are not particularly limited insofar as the silicone-modified water-absorbing polymer particles are not directly contacted with water, and may be water-in-oil or oil-in-water emulsified cosmetics, oil cosmetics, spray cosmetics and stick-type cosmetics. The type of the cosmetics of this invention is not particularly limited, and the cosmetics of this invention include skin cosmetics such as a pack, foundation, lipstick, lotion, cold cream, hand cream, skin detergent, softening cosmetics, nutrient cosmetics, astringent cosmetics, whitening cosmetics, wrinkle-improving cosmetics, aging-preventing cosmetics, cleansing cosmetics, sweat regulator and deodorant; and hair cosmetics such as a rinse, treatment, hair-dressing, hair tonic, styling agent and hair feel improver.

Among these, the cosmetics of this invention are preferably used as antiperspirant and deodorant, or preferably used together with another sweating regulator. The antiperspirant includes aluminum salts such as allantoin chlorohydroxy aluminum, aluminum chloride, chlorohydroxy aluminum, allantoin dihydroxy aluminum, aluminum sulfate, potassium alum and aluminum hydroxide, aluminum-zirconium complexes such as aluminum zirconium tetrachlorohydroxy glycine and aluminum zirconium pentachlorohydrate, zinc salts such as zinc oxide and zinc p-phenol sulfonate, and salicylic acid, tannic acid etc. Among these, allantoin chlorohydroxy aluminum, aluminum chloride, chlorohydroxy aluminum and aluminum hydroxide are particularly preferable. The amount of the antiperspirant incorporated is preferably 0.01 to 15% by weight, particularly preferably 0.1 to 5% by weight in the sweat regulator.

By further incorporating silicone oil into the cosmetics of this invention, the resultant cosmetics can give dry feeling for use with a reduction in sticky feeling. Such silicone oil is not particularly limited, but the one having a viscosity (25° C.) of at most 50 mm$^2$/s can be preferably used. This is because if silicone oil is used in a larger amount to increase viscosity, the polymer particles feel oily and are not preferable in feeling for use. For example, linear silicones such as low-polymerized dimethyl polysiloxane and methyl phenyl polysiloxane, and octamethyl cyclotetrasiloxane, decamethyl cyclopentasiloxane etc. can be suitably selected and used singly or in combination thereof if necessary. The silicone oil is incorporated in an amount of preferably 0.01 to 5% by weight, particularly preferably 0.1 to 1% by weight in the cosmetics of this invention.

Preferably, the cosmetics of this invention further contain alcohol in order to give dry feeling. Such alcohol includes $C_{1-6}$ monohydric or polyhydric alcohols such as ethanol, glycerin, 1,3-butylene glycol, propylene glycol and sorbitol. In particular, a monohydric alcohol, particularly ethanol is preferable. The amount of the alcohol incorporated is preferably 5 to 30% by weight in the cosmetics of this invention, particularly preferably 2 to 50 parts times by weight of the silicone-modified water-absorbing polymer particles.

Depending on the form, type etc. of the cosmetics, other conventional components can be further incorporated as cosmetic components into the cosmetics of this invention in such a range that the effect of this invention is not hindered.

Such cosmetic components include e.g. extender pigments such as mica, talc, sericite, kaolin, nylon powder, polymethylsilyl sesquioxane and barium sulfate; inorganic pigments such as titanium oxide, zinc white and iron oxide; powders whose surface was rendered hydrophobic by treating these powders with silicone, metal soap or N-acyl glutamic acid; hydrocarbons such as solid or liquid paraffin, solid paraffin, microcrystalline wax, vaseline, ceresin, ozokerite and montan wax; vegetable or animal fats and oils or wax, such as olive, ozokerite, carnauba wax, lanoline and spermaceti; fatty acids or esters thereof such as stearic acid, palmitic acid, oleic acid, glycerine monostearate, glycerine distearate, glycerine monooleate, isopropyl myristate, isopropyl stearate and butyl stearate; higher alcohols such as cetyl alcohol, stearyl alcohol, palmityl alcohol and hexyl dodecyl alcohol; adsorbents or thickening agents such as cationic cellulose, carboxybetaine type polymer and cationic silicone; polyhydric alcohols having a moisture retention action, such as glycol and sorbitol; efficacious components such as whitening agent, analgesic antiinflammatory agents, anti-itching agents, sterilizing disinfectants, astringents, skin softening agents and hormones; water; surfactants; W/O or O/W type emulsifying agents; emulsifying agents for silicone oil, such as polyether-modified silicone, polyether alkyl-modified silicone and glyceryl ether-modified silicone; thickening agents such as methyl cellulose, ethyl cellulose, carboxymethyl cellulose, polyacrylic acid, tragacanth, agar and gelatin; and other components such as emulsion stabilizer, chelating agents, UV protecting agents, pH adjusting agents, preservatives, coloring matters and perfumes.

The cosmetics of this invention are produced according to a conventional method.

The silicone-modified water-absorbing polymer particles of this invention comprise water-absorbing polymer particles coated thereon via chemical bonding, with a silicone compound having at least one kind of functional group. Unlike silicone oil simply mixed in water-absorbing polymer particles, the silicone compound is stably present on the surfaces of the water-absorbing polymer particles even after incorporated into cosmetics. The silicone-modified water-absorbing polymer particles of this invention, upon absorption of water, exhibit a significant reduction in sticky feeling and gel blocking (phenomenon of forming lumps) attributable to the fusing ability of the surfaces of the polymer particles, and when used as cosmetics, the polymer particles have preferable feeling in use.

EXAMPLE

[Method of Measuring the Amount of Water Absorbed]

1000 ml water was added to 5 g sample which was then suspended and stirred for 30 minutes (100 rpm, 25° C.) and centrifuged at 2,000 G for 30 minutes, and the supernatant was gently discarded, and the weight of the sample was measured. On the basis of the difference of this weight from the initial weight of the sample, the amount of water absorbed was determined.

[Method of Evaluating a Deodorizing Ability]

(1) A 7 cm×6 mm scent paper (perfume test paper, produced by Daimonji Yoshi Co., Ltd.) is coated (about 1 cm$^2$) with 150 mg silicone-modified polymer particles (5% by weight in water).

(2) Then, the same scent paper is impregnated with 50 mg bad-smelling solution [model smell (0.005% aqueous isovaleric acid solution)].

(2) The scent paper having the bad smell+the deodorant is placed in a 3-L beaker which is then sealed with Saran Wrap (trade name), left for 20 minutes (20° C.), and the smell filled in the beaker is by sensory test evaluated. As the reference, the scent paper having only the bad smell in a beaker is also prepared.

Smell evaluation:
⊚: Odorless or with unspecified smell
○: Slightly smells.
Δ: Apparently smells.
×: Strongly smells.

[Method of Evaluating Feeling in Use (When Dried)]

0.2 g sample was applied onto the forearm, then evaluated by sensory test for the extendability and dry and smooth feeling of the powder, and scored according to the following criteria.
5: Does not feel sticky, spreads very well and feels very dry and smooth.
4: Spreads well and feels dry and smooth.
3: Feels slightly sticky and slightly poor in spreading.
2: Poor in spreading, and feels gritty or sticky.
1: Very poor in spreading and feels very gritty or sticky.

[Method of Evaluating Feeling in Use (When Sweating)]

0.2 g sample was applied onto the forearm, evaluated by sensory test for stickiness and dry feeling after 30 minutes in a room with 75% RH at 40° C., and scored according to the following criteria:
5: Does not feel sticky, spreads very well and feels very dry.
4: Spreads well and feels dry.
3: Feels slightly sticky and slightly poor in spreading.
2: Poor in spreading and feels slimy or sticky.
1: Very poor in spreading and feels very slimy or sticky.

Example 1

300 g methacrylic acid (Mitsubishi Rayon Co., Ltd.) and 135 g deionized water were placed in a 3-L beaker and then neutralized to a degree of 75% by adding 348 g of 30 weight % aqueous sodium hydroxide solution dropwise thereto under cooling with stirring, and then a solution of 1.2 g potassium persulfate (0.4% by weight relative to methacrylic acid) dissolved in 24.3 g deionized water and 15.0 g of a crosslinking agent ethylene glycol diglycidyl ether (trade name, Denacol EX810, Nagase Kasei Co., Ltd.) (5.0% by weight relative to methacrylic acid) were added thereto, and the mixture was uniformly dissolved. The resultant solution was added to a solution obtained by dissolving 15 g amino-modified silicone A (XF42-703 produced by Toshiba Silicones; viscosity (25° C.), 1000 mm$^2$/s; amine equivalent, 1500 g/mol) in 1500 ml cyclohexane in a 3-L beaker, and the mixture was stirred vigorously for 5 minutes at a number of revolutions of 10000 rpm in a homomixer to produce a fine water-in-oil droplet dispersion. Then, 900 ml cyclohexane was introduced into a 5-L stainless steel reaction vessel equipped with a reflux condenser, stirred at 350 rpm, and heated at 75° C. in the system, and the atmosphere was replaced by nitrogen, followed by dropwise addition of the partially neutralized water-in-oil droplet dispersion of methacrylic acid to initiate polymerization. The whole of the droplet dispersion was added dropwise over 1.5 hours, and the reaction solution was kept for additional 4 hours at the reflux temperature. Thereafter, a dehydration tube was attached, the temperature was raised to remove 340 ml water, and the reaction solution was cooled and filtered to separate polymer particles. By evaporation into dryness under reduced pressure, 376 g dry white polymer in the form of fine powder was obtained. The average particle diameter of the resultant fine polymer particles was 2.2 μm. A photograph by SEM (scanning electron microscope) of the silicone-modified polymer particles in a dry state obtained in Example 1 is shown in FIGS. 1 and 2.

Examples 2 to 5

Using the monomers, dispersants and crosslinking agents in Table 1, fine polymer particles were obtained according to the method in Example 1.

Example 6

300 g methacrylic acid (Mitsubishi Rayon Co., Ltd.) and 135 g deionized water were placed in a 3-L beaker and then neutralized to a degree of 75% by adding 348 g of 30 weight % aqueous sodium hydroxide solution dropwise thereto under cooling with stirring, and then a solution of 1.2 g potassium persulfate (0.4% by weight relative to methacrylic acid) dissolved in 24.3 g deionized water was added thereto, and the mixture was dissolved uniformly. The resultant solution was added to a solution obtained by dissolving 15 g amino-modified silicone A (viscosity (25 C), 1000 mm$^2$/s; amine equivalent, 1500 g/mol) in 1500 ml cyclohexane in a 3-L beaker, and the mixture was stirred vigorously for 5 minutes at a number of revolutions of 10000 rpm in a homomixer to produce a fine water-in-oil droplet dispersion. Then, 900 ml cyclohexane was introduced into a 5-L stainless steel reaction vessel equipped with a reflux condenser, and stirred at 350 rpm and heated at 75° C. in the system, and the atmosphere was replaced by nitrogen, followed by dropwise addition of the partially neutralized water-in-oil droplet dispersion of methacrylic acid to initiate polymerization. The whole of the droplet dispersion was added dropwise over 1.5 hours, and the reaction solution was kept for additional 4 hours at the reflux temperature. Thereafter, a dehydration tube was attached, the temperature was raised to remove 300 ml water, and then a solution of 3.0 g of a crosslinking agent ethylene glycol diglycidyl ether (trade name, Denacol EX810, Nagase Kasei Co., Ltd.) (1.0% by weight relative to methacrylic acid) dissolved in 20 g deionized water was added dropwise thereto for 5 minutes. After aging for 1 hour, 1300 ml cyclohexane was evaporated, and the reaction solution was left and cooled to complete synthesis. By evaporation into dryness under reduced pressure, 380 g dry white polymer in the form of fine powder was obtained. The average particle diameter of the resultant fine polymer particles was 2.9 μm.

Example 7

300 g methacrylic acid (Mitsubishi Rayon Co., Ltd.) and 135 g deionized water were placed in a 3-L beaker and then neutralized to a degree of 75% by adding 348 g of 30 weight % aqueous sodium hydroxide solution dropwise thereto under cooling with stirring, and then a solution of 1.2 g potassium persulfate (0.4% by weight relative to methacrylic acid) dissolved in 24.3 g deionized water and 9.0 g of a crosslinking agent ethylene glycol diglycidyl ether (trade name, Denacol EX810, Nagase Kasei Co., Ltd.) (3.0% by weight relative to methacrylic acid) were added thereto, and the mixture was uniformly dissolved. The resultant solution was added to a solution obtained by dissolving 15 g amino-modified silicone A (viscosity (25° C.), 1000 mm$^2$/s; amine equivalent, 1500 g/mol) in 1500 ml cyclohexane in a 2-L beaker, and the mixture was stirred in a homomixer such that the particle diameter of monomer droplets was reduced to about 50 μm, to produce a fine water-in-oil droplet dispersion.

Then, 900 ml cyclohexane was introduced into a 5-L stainless steel reaction vessel equipped with a reflux condenser, then stirred at 350 rpm and heated at 75° C. in the system, and the atmosphere was replaced by nitrogen, followed by dropwise addition of the partially neutralized water-in-oil droplet dispersion of methacrylic acid to initiate polymerization. The whole of the droplet dispersion was added dropwise over 1.5 hours, and the reaction solution was aged for additional 4 hours at the reflux temperature. Thereafter, a dehydration tube was attached, the temperature was raised to remove 340 ml water, and 1300 ml cyclohexane was evaporated, and the reaction solution was left and cooled to complete synthesis. By evaporation into dryness under reduced pressure, 357 g dry white polymer in the form of fine powder was obtained. The average particle diameter of the resultant fine polymer particles was 50 µm.

Example 8

300 g methacrylic acid (Mitsubishi Rayon Co., Ltd.) and 135 g deionized water were placed in a 3-L beaker and then neutralized to a degree of 75% by adding 348 g of 30 weight % aqueous sodium hydroxide solution dropwise thereto under cooling with stirring, and then a solution of 1.2 g potassium persulfate (0.4% by weight relative to methacrylic acid) dissolved in 24.3 g deionized water was added thereto, and the mixture was uniformly dissolved. Then, 1500 ml cyclohexane and 15 g of amino-modified silicone C (KF-861 produced by Shin-Etsu Silicones; viscosity (25° C.), 3500 mm$^2$/s; amine equivalent, 2000 g/mol) were introduced into a 5-L stainless steel reaction vessel equipped with a reflux condenser, and heated at 75° C. in the system, and the atmosphere was replaced by nitrogen, followed by dropwise addition of the aqueous partially neutralized methacrylic acid solution to initiate polymerization. The whole of the solution was added dropwise over 1.5 hours, and the reaction solution was aged for additional 4 hours at the reflux temperature. Thereafter, a dehydration tube was attached, the temperature was raised to remove 300 ml water, and then a solution of 3.0 g of a crosslinking agent ethylene glycol diglycidyl ether (trade name, Denacol EX810, Nagase Kasei Co., Ltd.) (1.0% by weight relative to methacrylic acid) dissolved in 20 g deionized water was added dropwise thereto for 5 minutes. The reaction solution was heated to remove 340 ml water, left and cooled to complete synthesis. By evaporation into dryness under reduced pressure, 364 g dry white polymer in the form of fine powder was obtained. The average particle diameter of the resultant fine polymer particles was 230 µm.

Comparative Example 1

300 g methacrylic acid (Mitsubishi Rayon Co., Ltd.) and 135 g deionized water were placed in a 3-L beaker and neutralized to a degree of 75% by adding 348 g of 30 weight % aqueous sodium hydroxide solution dropwise thereto under cooling with stirring, and then a solution of 1.2 g potassium persulfate (0.4% by weight relative to methacrylic acid) dissolved in 24.3 g deionized water and 15.0 g of a crosslinking agent ethylene glycol diglycidyl ether (trade name, Denacol EX810, NagaseKasei Co., Ltd.) (5.0% by weight relative to methacrylic acid) were added thereto, and the mixture was uniformly dissolved. The resultant solution was added to a solution obtained by dissolving 15 g sugar esters (a mixture of Ryoto Sugar Esters S570 and S770 (trade name) in equal amounts, Mitsubishi Shokuhin Co., Ltd.) (5.0% by weight relative to methacrylic acid) as a dispersion stabilizer in 1500 ml cyclohexane in a 3-L beaker, and the mixture was stirred vigorously for 5 minutes at a number of revolutions of 10000 rpm in a homomixer to produce a fine water-in-oil droplet dispersion. Then, 900 ml cyclohexane was introduced into a 5-L stainless steel reaction vessel equipped with a reflux condenser, and stirred at 350 rpm and heated at 75° C. in the system, and the atmosphere was replaced by nitrogen, followed by dropwise addition of the partially neutralized water-in-oil droplet dispersion of methacrylic acid to initiate polymerization. The whole of the droplet dispersion was added dropwise over 1.5 hours, and the reaction solution was aged for additional 4 hours at the reflux temperature. Thereafter, a dehydration tube was attached, the temperature was raised to remove 340 ml water, further 1300 ml cyclohexane was evaporated, and the reaction solution was left and cooled to complete synthesis. By evaporation into dryness under reduced pressure, 376 g dry white polymer in the form of fine powder was obtained. The average particle diameter of the resultant dry fine polymer particles was 2.2 µm.

Example 9

372 g of the fine water-absorbing polymer particles obtained in Comparative Example 1 were added to 2000 ml cyclohexane and 15 g amino-modified silicone D (KF-864 produced by Shin-Etsu Silicones; viscosity (25° C.), 1700 mm$^2$/s; amine equivalent, 3800 g/mol) (4% by weight relative to the water-absorbing polymer), and the system was heated at 75° C. with stirring at 350 rpm for 30 minutes. Then, 150 g deionized water was added dropwise, the mixture was further stirred at 75° C. for 30 minutes, and a solution of 3.0 g crosslinking agent ethylene glycol diglycidyl ether (trade name, Deconal EX810, Nagase Kasei Co., Ltd.) (0.8% by weight relative to the water-absorbing polymer) dissolved in 20 g deionized water was added dropwise over 5 minutes. The mixture was further aged for 4 hours at the reflux temperature, and after a dehydrating tube was attached, the reaction temperature was raised to remove 100 ml water, and the reaction solution was left and cooled to complete synthesis. By evaporation into dryness under reduced pressure, 375 g dry white polymer in the form of fine powder was obtained. The average particle diameter of the resultant fine polymer particles was 2.4 µm.

Example 10

180 g of a solution of a quarternized product of dimethylaminoethylmethacrylatewithdiethylsulfuric acid, including 90% of the effective component, 120 g of N,N-dimethylacrylamide, 14 g of polyethylene glycol dimethacrylate, NK-14G (tradename of ShinNakamura Chemical Co., Ltd.), 5 g of methacrylic acid, 415 g of deionized water and 1.2 g of potassium persulfate were introduced in a 3-L beaker and dissolved uniformly. The obtained solution was added in a 3-L beaker to a solution obtained by dissolving 15 g amino-modified siliconeA, XF42-703 producedbyToshiba Silicones, having viscosity (25° C.) of 1000 mm$^2$/s and amine equivalent of 1500 g/mol, in 1500 ml of cyclohexane. The mixture was stirred vigorously for 5 minutes at a number of revolutions of 10000 rpm in a homomixer to produce a fine water-in-oil droplet dispersion. The water-in-oil droplet dispersion was introduced into a 5-L stainless steel reaction vessel equipped with a reflux condenser, stirred at 350 rpm. Purged by nitrogen gas, it was heated at 75° C. and it was kept for 4 hours for polymerization. Thereafter, a dehydration tube was attached, the temperature was raised to remove 340 ml water and the reaction solution was cooled and filtered to separate polymer particles. By evaporation into dryness at a reduced pressure, 280 g dry white polymer in the form of fine powder was obtained. The average particle diameter of the resultant fine polymer particles was 2.5 μm.

Example 11

300 g of N,N-dimethylacrylamide, 4.5 g of polyethylene glycol dimethacrylate, NK-14G (tradename of ShinNakamura Chemical Co., Ltd.), 5 g of methacrylic acid, 400 g of deionized water and 1.2 g of potassium persulfate were introduced in a 3-L beaker and dissolved uniformly. The obtained solution was added in a 3-L beaker to a solution obtained by dissolving 15 g amino-modified silicone A, XF42-703 produced by Toshiba Silicones, having viscosity (25° C.) of 1000 mm$^2$/s and amine equivalent of 1500 g/mol, in 1500 ml of cyclohexane. The mixture was stirred vigorously for 5 minutes at a number of revolutions of 10000 rpm in a homomixer to produce a fine water-in-oil droplet dispersion. The water-in-oil droplet dispersion was introduced into a 5-L stainless steel reaction vessel equipped with a reflux condenser, stirred at 350 rpm. Purged by nitrogen gas, it was heated at 75° C. and it was kept for 4 hours for polymerization. Thereafter, a dehydration tube was attached, the temperature was raised to remove 340 ml water and the reaction solution was cooled and filtered to separate polymer particles. By evaporation into dryness at a reduced pressure, 290 g dry white polymer in the form of fine powder was obtained. The average particle diameter of the resultant fine polymer particles was 2.3 μm.

Example 12

300 g methacrylic acid (Mitsubishi Rayon Co., Ltd.) and 135 g deionized water were introduced in a 3-L beaker and then neutralized to a degree of 75% by adding 348 g of 30 weight-% aqueous sodium hydroxide solution dropwise thereto, while cooled and stirred. Then a solution of 1.2 g potassium persulfate, being 0.4% by weight relative to methacrylic acid, dissolved in 24.3 g of deionized water and 15.0 g of a crosslinking agent of ethylene glycol diglycidyl ether, Denacol EX810 (trade name by Nagase Kasei Co., Ltd.), being 5.0% by weight relative to methacrylic acid, were added thereto. The mixture was uniformly dissolved. The resultant solution was added in a 3-L beaker to a solution obtained by dissolving 15 g of hydroxy-modified silicone having the formula (1), disclosed in JP-A 5-112424, Production Example-7, in 1500 ml cyclohexane. The mixture was stirred vigorously for 5 minutes at a number of revolutions of 10000 rpm in a homomixer to produce a fine water-in-oil droplet dispersion. Then, 900 ml cyclohexane was introduced into a 5-L stainless steel reaction vessel equipped with a reflux condenser, stirred at 350 rpm and heated at 75° C. in the system. Having been replaced by nitrogen, the partially neutralized water-in-oil droplet dispersion of methacrylic acid was added dropwise thereto to initiate polymerization. The whole of the droplet dispersion was added dropwise over 1.5 hours and the reaction solution was kept for additional 4 hours at the reflux temperature. Thereafter, a dehydration tube was attached, the temperature was raised to remove 340 ml water, and the reaction solution was cooled and filtered to separate polymer particles. By evaporation into dryness under reduced pressure, 355 g of dry white polymer in the form of fine powder was obtained. The average particle diameter of the resultant fine polymer particles was 1.8 μm.

$m = 60, n = 4$

Example 13

180 g of a solution of a quaternized product of dimethylaminoethyl methacrylate with diethylsulfuric acid, including 90% of the effective component, 120 g of N,N-dimethylacrylamide, 14 g of polyethylene glycol dimethacrylate, NK-14G (tradename of ShinNakamura Chemical Co., Ltd.), 415 g of deionized water and 1.2 g of potassium persulfate were introduced in a 3-L beaker and dissolved uniformly. The obtained solution was added in a 3-L beaker to a solution obtained by dissolving 15 g carboxy-modified silicone, produced by JP-A 2002-114849, Example 1, being a condensate of aminoethylaminopropyl-modified silicone, KF-869 (tradename of Shinetsu Chemical Co., Ltd.) with succinic anhydride, having a succinic anhydride-modified extent of 93%, in 1500 ml of cyclohexane. The mixture was stirred vigorously for 5 minutes at a number of revolutions of 10000 rpm in a homomixer to produce a fine water-in-oil droplet dispersion. The water-in-oil droplet dispersion was introduced into a 5-L stainless steel reaction vessel equipped with a reflux condenser, stirred at 350 rpm. Purged by nitrogen gas, it was heated at 75° C. and it was kept for 4 hours for polymerization. Thereafter a dehydration tube was attached, the temperature was raised to remove 340 ml water and the reaction solution was cooled and filtered to separate polymer particles. By evaporation into dryness at a reduced pressure, 285 g dry white polymer in the form of fine powder was obtained. The average particle diameter of the resultant fine polymer particles was 3.0 μm.

Comparative Example 2

255 g of 80 weight % industrial acrylic acid and 135 g deionized water were placed in a 3-L beaker and then neutralized to a degree of 75% by adding 284 g of 30 weight % aqueous caustic sodium solution dropwise thereto under cooling with stirring, and then a solution of 0.8 g potassium persulfate (0.4% by weight relative to methacrylic acid) dissolved in 20 g deionized water and 0.1 g of a crosslinking agent ethylene glycol diglycidyl ether (trade name, Deconal EX810, Nagase Kasei Co., Ltd.) (0.05% by weight relative to acrylic acid) were added thereto, and the mixture was uniformly dissolved. Then, 1000 ml cyclohexane and 10.2 g of ethyl cellulose (trade name, N-100, produced by Hercules Ltd.) were introduced into a 5-L stainless steel reaction vessel equipped with a reflux condenser, and the mixture was stirred at 450 rpm and heated at 75° C. in the system, and the atmosphere was replaced by nitrogen, followed by dropwise addition of the aqueous partially neutralized acrylic acid solution to initiate polymerization. The whole of the solution was added dropwise over 1.5 hours, and the reaction solution was aged for additional 4 hours at the reflux temperature. Thereafter, a dehydration tube was attached, the temperature was raised to remove 250 ml water, and the reaction solution was left and cooled to complete synthesis. By evaporation into dryness under reduced pressure, 250 g dry white polymer in the form of powder was obtained. The average particle diameter of the resultant dry fine polymer particles was 250 μm.

Comparative Example 3

0.1 g dimethyl polysiloxane (50 mm$^2$/s), TSF-451-50A produced by GE Toshiba Silicones Co., Ltd., was added to and sufficiently mixed with 100 g of the dry white polymer obtained in Comparative Example 1.

Comparative Example 4

0.1 g polyethylene oxide-modified silicone oil (KF351A produced by Shin-Etsu Silicones) was added to and mixed sufficiently with 100 g of the dry white polymer obtained in Comparative Example 1.

30 g polymer particles obtained in each of Example 1 Comparative Examples 3 and 4 were washed 3 times by stirring in 300 ml chloroform (50° C., 30 rpm, 2 hours) and subsequent centrifugation.

IPC elemental analysis indicated that in the polymer particles in Example 1, silicon atoms were detected both before and after washing. In the polymer particles in Comparative Examples 3 and 4, silicone atoms could not be detected.

By ESCA (x-ray electron spectroscopy for chemical analysis), it was found that silicone atoms are present in the vicinity of the surfaces of the polymer particles in Example 1. Further, the polymer particles in Examples 1 to 9 and Comparative Examples 1 and 2 were evaluated for the amount of absorbed water, the deodorizing ability, and the feeling in use (when dry and sweating), and the results are shown in Table 1.

<Determination of the Amount of the Modified-silicone Immobilized on the Polymer Particles>

10 g of polymer particles of Example 6, using 5.0 wt. %, per methacrylic acid, of the amino-modified silicone, was obtained by the polymerization, cooling and drying at a reduced pressure without filtration and was extracted by a soxhlet extractor with 400 ml of chloroform at 70° C. for 4 hours. The amino-modified silicone of the extract was determined by $^1$H-NMR. It was calculated that the amount of the amino-modified silicone, not having been extracted out, but remaining immobilized on the polymer particles, was 3.0 wt. per methacrylic acid.

<Determination of Particle Diameter>

The polymer particles obtained in Example was added to cyclohexane and treated with ultrasonic waves to prepare the fine particle dispersion. It was determined in view of particle diameter with a size distribution measuring device of laser diffraction-scattering, LS230 (tradename of Horiba, Ltd.) at the relative refraction index of 1.10, provided that the polymer particles had the refraction index of 1.57 and cyclohexane had that of 1.43. The obtained median was taken as an average particle diameter. The particle diameter distribution was obtained by dividing the standard deviation with the average particle diameter.

The silicone-modified water-absorbing polymer particles (salts) polymerized from methacrylic acid monomers showed a significant deodorizing effect by neutralization of the short-chain carboxylic acid as a cause of bad smell.

TABLE 1

| | | | | Examples | | | | |
|---|---|---|---|---|---|---|---|---|
| | | | | 1 | 2 | 3 | 4 | 5 |
| Starting materials | monomer | Type | | Sodium methacrylate | Sodium methacrylate | potassium acrylate | Sodium methacrylate | Sodium methacrylate |
| | | Degree of neutralization | | 75% | 75% | 75% | 75% | 75% |
| | Dispersant | Type | | amino-modified silicone A | amino-modified silicone B | amino-modified silicone A | amino-modified silicone C | amino-modified silicone A |
| | | Added amount | | 5 weight % | 2 weight % | 5 weight % | 5 weight % | 5 weight % |
| | Surface-treating agent | Type | | — | — | — | — | — |
| | | Added amount | | — | — | — | — | — |
| | Cross-linking agent | Type | | EGDGE (EX810) | EGDGE (EX810) | PGPGE (EX512) | EGDGE (EX810) | PEGDMA (NK-9G) |
| | | Added amount | | 5 weight % | 1 weight % | 1 weight % | 5 weight % | 3 weight % |
| Polymers | | yield | | 97% | 95% | 95% | 97% | 97% |
| | | Average particle diameter | | 2.2 μm | 2.3 μm | 2.1 μm | 2.7 μm | 2.2 μm |
| | | Distribution of particle diameter | | 0.45 | 0.47 | 0.43 | 0.53 | 0.45 |
| | | Amount of water absorbed | | 15 g/g | 75 g/g | 95 g/g | 20 g/g | 110 g/g |
| Evaluation | | Deodorizing ability | | ◎ | ◎ | ○ | ◎ | ◎ |
| | Feeling in use | when dry | | ◎ | ◎ | ◎ | ◎ | ◎ |

TABLE 1-continued

| | | | Examples | | | | |
|---|---|---|---|---|---|---|---|
| | | | | | | | 9 |
| | | | 6 | 7 | 8 | polymerization | After polymerization (post-treatment) |
| Starting materials | monomer | Type | Sodium methacrylate | Sodium methacrylate | Sodium methacrylate | Sodium methacrylate | — |
| | | Degree of neutralization | 75% | 75% | 75% | 75% | — |
| | Dispersant | Type | amino-modified silicone A | amino-modified silicone A | amino-modified silicone C | Sugar ester | — |
| | | Added amount | 5 weight % | 5 weight % | 5 weight % | 5 weight % | — |
| | Surface-treating agent | Type | — | — | — | — | amino-modified silicone D |
| | | Added amount | — | — | — | — | 4 weight % |
| | Cross-linking agent | Type | EGDGE (EX810) | EGDGE (EX810) | EGDGE (EX810) | EGDGE (EX810) | EGDGE (EX810) |
| | | Added amount | 1 weight % | 3 weight % | 1 weight % | 5 weight % | 0.8 weight % |
| Polymers | | yield | 98% | 92% | 94% | 97% | |
| | Average particle diameter | | 2.9 μm | 50 μm | 230 μm | 2.4 μm | |
| | Distribution of particle diameter | | 0.5 | 0.45 | 0.57 | 0.57 | |
| | Amount of water absorbed | | 95 g/g | 55 g/g | 350 g/g | 13 g/g | |
| Evaluation | Deodorizing ability | | ⊚ | ⊚ | ○ | ⊚ | |
| | Feeling in use | when dry | ⊚ | ⊚ | ○ | ⊚ | |
| | | when swollen | ⊚ | ○ | ○ | ⊚ | |

| | | | | Comparative examples | |
|---|---|---|---|---|---|
| | | | | 1 | 2 |
| Starting materials | monomer | Type | | Sodium methacrylate | sodium acrylate |
| | | Degree of neutralization | | 75% | 75% |
| | Dispersant | Type | | Sugar ester | Ethyl cellulose |
| | | Added amount | | 5 weight % | 5 weight % |
| | Surface-treating agent | Type | | — | — |
| | | Added amount | | — | — |
| | Cross-linking agent | Type | | EGDGE (EX810) | EGDGE (EX810) |
| | | Added amount | | 5 weight % | 0.05 weight % |
| Polymers | | yield | | 93% | 92% |
| | Average particle diameter | | | 2.2 μm | 250 μm |
| | Distribution of particle diameter | | | 0.58 | 0.61 |
| | Amount of water absorbed | | | 12 g/g | 350 g/g |
| Evaluation | Deodorizing ability | | | ○ | Δ |
| | Feeling in use | when dry | | ○ | Δ |
| | | when swollen | | Δ | × |

TABLE 2

|  |  |  | Example 10 | Example 11 | Example 12 | Example 13 |
|---|---|---|---|---|---|---|
| starting material | monomer | type | diethylsulfuric acid-quaternized product of dimethylaminoethylmethacrylate N,N-dimethylacry amide methacrylic acid | N,N-dimethylacry amide methacrylic acid | methacrylic acid | diethylsulfuric acid-quaternized product of dimethylaminoethylmethacrylate N,N-dimethylacry amide |
|  |  | netralization |  |  | 75% |  |
|  | dispersant | type | amino-modified silicone A | amino-modified silicone A | hydroxy-modified silicone | carboxy-modified silicone |
|  |  | added amount | 5.3 wt % | 4.9 wt % | 5.0 wt % | 5.3 wt % |
|  | cross-linking agent | type | PEGDMA(NK-14G) | PEGDMA(NK-14G) | EGDGE(DenacolEX810) | PEGDMA(NK-14G) |
|  |  | added amount | 5 wt % | 1.5 wt % | 5.0 wt % | 5.0 wt % |
| polymer |  | yield | 93% | 94% | 92% | 93% |
|  |  | average diameter | 2.5 μm | 2.3 μm | 1.8 μm | 1.8 μm |
|  |  | distribution of diameter | 0.48 | 0.52 | 0.59 | 0.62 |
|  |  | amount of water absorbed | 18 g/g | 18 g/g | 11 g/g | 18 g/g |
| evaluation | deodora |  | — | — | ○ | — |
|  | feeling in use | when dry | ◎ | ◎ | ○ | ○ |
|  |  | when swelled | ○ | ○ | ○ | ○ |

(Note)
*Addition amount: Expressed in the weight ratio thereof to the monomer (during reaction) or in the weight ratio to the water-absorbing polymer particles (after polymerization or during post-treatment)
*EGDGE: ethylene glycol diglycidyl ether, and EX810 is Denacol EX810, manufactured by Nagase Chemical Co., Ltd.
*PGPGE: polyglycerol polyglycidyl ether, and EX512 is Denacol EX512 (Nagase Kasei Co., Ltd.).
*PEGDMA: polyethylene glycol dimethacrylate. NK-9G and NK-14G are polyethylene glycol dimethacrylate having n = 9 and n = 14, respectively, n being the polymerization degree of polyethylene glycol, manufactured by Shin-Nakamura Chemical Co., Ltd.
*Amino-modified silicone A: XF42-703, viscosity (25° C.) 1000 mm$^2$/s, amine equivalent 1600 g/mol, produced by GE Toshiba Silicones Co., Ltd..
*Amino-modified silicone B: KF-867, viscosity (25° C.) 1300 mm$^2$/s, amine equivalent 1700 g/mol, produced by Shin-Etsu Silicones.
*Amino-modified silicone C: KF-861, viscosity (25° C.) 3500 mm$^2$/s, amine equivalent 2000 g/mol, produced by Shin-Etsu Silicones.
*Amino-modified silicone D: KF-864, viscosity (25° C.) 1700 mm$^2$/s, amine equivalent 3800 g/mol, produced by Shin-Etsu Silicones.

Formulation Example 1 and 2 and Comparative Formulation Examples 1 and 2 (Sweat-regulating Sticks)

The ingredients a) to f) in Table 3 were uniformly mixed under heating and introduced into a container, left and cooled to give sweat-regulating sticks. The evaluation results are shown in Table 3.

Formulation Example 3 and Comparative Formulation Example 3 (Sweat-regulating Body Powder)

The ingredients a) to f) in Table 4 were uniformly mixed by a Henschel mixer, and introduced into a container to give sweat-regulating body powder. The evaluation results are shown in Table 4.

TABLE 3

|  |  |  | Formulation Example 1 | Formulation Example 2 | Comparative Formulation Example 1 | Comparative Formulation Example 2 |
|---|---|---|---|---|---|---|
| Composition (weight %) | a) | Octamethyl cyclotetrasiloxan | 34.0 | 34.0 | 34.0 | 34.0 |
|  | b) | Dimeticone 6cs | 34.0 | 34.0 | 34.0 | 34.0 |
|  | c) | Paraffin wax | 12.0 | 12.0 | 12.0 | 12.0 |
|  | d) | Water-absorbing polymer in Example 2 | 20.0 | 18.0 | — | — |
|  | e) | Water-absorbing polymer in Comparative Example 1 | — | — | 20.0 | 18.0 |
|  | f) | Aluminum zirconium chlorohydrex glycine | — | 2.0 | — | 3.0 |
| Feeling in use (when dry) |  |  | 5 | 5 | 4 | 2 |
| Feeling in use (when swollen) |  |  | 4 | 5 | 2 | 1 |

* Dimeticone 6cs: KF96-6cs produced by Shin-Etsu Silicones
* Paraffin wax: HNP-9 produced by Nihon Seiroh

TABLE 4

|   | | Formulation Example 3 | Comparative Formulation Example 3 |
|---|---|---|---|
| Composition (weight %) | | | |
| a) | Aluminum chlorohydrate | 5.00 | 5.00 |
| b) | Triclosan | 0.01 | 0.01 |
| c) | Water-absorbing polymer in Example 2 | 20.0 | — |
| d) | Water-absorbing polymer in Comparative Example 1 | — | 20.0 |
| e) | Talc | Balance | Balance |
| f) | Perfume | Suitable amount | Suitable amount |
|   | Total | 100.0 | 100.0 |
| Feeling in use (when dry) | | 5 | 3 |
| Feeling in use (when sweating) | | 4 | 1 |

Formulation Example 4 (Powder Spray)

The following ingredients a) to c) were mixed in a kneader, and d) and e) were mixed by a blender, and these were charged into a spray container, and further f) and g) were charged into the spray container, to give a powder spray. The resultant powder spray was scored rank 5 for feeling in use when dry, and rank 4 for feeling in use when sweating.

| a) | Water-absorbing polymer in Example 1 | 2.0 weight % |
|---|---|---|
| b) | Acryl polymer particles: Microsphere M305, 7 µm, manufactured by Matsumoto Oil and Fat Co., Ltd. | 1.0 weight % |
| c) | Talc | 0.5 weight % |
| d) | Isopropyl palmitinate | 1.5 weight % |
| e) | Perfume | 0.2 weight % |
| f) | Isopentane | 10.0 weight % |
| g) | Liquefied petroleum gas | balance |
|   | | (100.0 weight % in total) |

Formulation Example 5 (Compact Deodorant Powder)

The following ingredients a) to d) were mixed in a Henschel mixer, and ingredients d) and e) were added to this mixture which was then ground in a grinding device, placed on a middle dish and pressed to give a compact deodorant powder. The resultant compact deodorant powder was scored rank 5 for feeling in use when dry and rank 5 for feeling in use when sweating. Further, its deodorizing effect was confirmed.

| a) | Water-absorbing polymer in Example 5 | 50.0 weight % |
|---|---|---|
| b) | N-lauroyl lysine | 10.0 weight % |
| c) | Talc | 20.0 weight % |
| d) | Zinc oxide: FINEX-75, manufactured by Sakai Chemical Co., Ltd. | 10.0 weight % |
| d) | Dimeticone 20cs | 2.0 weight % |
| e) | Dimeticone 6cs | 8.0 weight % |

*Dimeticone 20cs: KF96-20cs produced by Shin-Etsu Silicones
*Dimeticone 6cs: KF96-6cs produced by Shin-Etsu Silicones Formulation Example 6 (Roll-on Type Sweat-regulating Agent)

The following ingredients a) to e) were mixed and introduced into a roll-on container to prepare a roll-on type sweat-regulating agent. The resultant roll-on type sweat-regulating agent was scored rank 4 for feeling in use when dry and rank 4 for feeling in use when sweating.

| a) | Octamethyl cyclotetrasiloxane | 65.0 weight % |
|---|---|---|
| b) | Dimeticone 6cs | 6.0 weight % |
| c) | Ethanol | 20.0 weight % |
| d) | Glycerin | 4.0 weight % |
| e) | Water-absorbing polymer in Example 6 | 5.0 weight % |

*Dimeticone 6cs: KF96-6cs produced by Shin-Etsu Silicones

Formulation Example 7 (Powder Foundation)

The following ingredients a) to e) were mixed in a Henschel mixer, and ingredients f) and i) which had been melted by heating were added thereto, mixed and ground. The resultant mixture was placed on a middle plate and pressed to give a powder foundation. The resultant powder foundation was scored rank 5 for feeling in use when dry and rank 5 for feeling in use when sweating, and this powder foundation was free of floating of the cosmetics with sweat, kept well in the cosmetics and excellent in usability.

| a) | Water-absorbing polymer in Example 4 | 5.0 weight % |
|---|---|---|
| b) | Zinc oxide: FINEX-75, manufactured by Sakai Chemical Co., Ltd. | 20.0 weight % |
| c) | Spherical silica: NP-30, 3 µm, manufactured by Asahi Glass Co., Ltd. | 25.0 weight % |
| d) | Mica | 15.0 weight % |
| e) | Talc | 25.0 weight % |
| f) | Coloring pigment | suitable amount |
| g) | Dimeticone 6cs | 3.0 weight % |
| h) | 2-Ethylhexyl p-methoxy cinnamate | 2.5 weight % |
| i) | Preservative suitable amount | (100.0 weight % in total) |

*Dimeticone 6cs: KF96-6cs produced by Shin-Etsu Silicones

Formulation Example 8 (Oily Foundation)

The following ingredients a) to i) were heated, melted and uniformly mixed by a blender, and ingredients j) to n) which had been mixed by a Henschel mixer were added thereto, and the mixture was kneaded by a roll mill. After the mixture was re-melted to regulate its color, and the perfume o) was added thereto at 60° C. thereto with stirring under degassing, and the mixture was poured into a container, then left and cooled to give an oily foundation. The resultant oily foundation was scored rank 4 for feeling in use when dry and rank 4 for feeling in use when sweating, and this powder foundation was free of floating of the cosmetics with sweat, kept well in the cosmetics and excellent in usability.

| a) | Octamethyl cyclotetrasiloxane | 25.0 weight % |
|---|---|---|
| b) | Dimeticone 6cs | 15.0 weight % |
| c) | Squalane | 5.0 weight % |
| d) | Alkyl-modified silicone wax: KF7002, manufactured by Shinetsu Silicone Co., Ltd. | 3.0 weight % |
| e) | Microcrystalline wax | 3.0 weight % |
| f) | Candelilla wax | 3.0 weight % |
| g) | Isopropyl palmitate | 3.5 weight % |
| h) | Preservative | suitable amount |
| i) | Antioxidant | suitable amount |
| j) | Titanium oxide: MT500R, manufactured by Teika Company | 15.0 weight % |

-continued

| | | |
|---|---|---|
| k) | Spherical silica: NP = 30, 3 μm, manufactured by Asahi Glass Co., Ltd. | 10.0 weight % |
| l) | Talc | 3.0 weight % |
| m) | Water-absorbing polymer in Example 4 | 3.0 weight % |
| n) | Coloring pigment | 5.0 weight % |
| o) | Perfume | suitable amount (100.0 weight % in total) |

*Dimeticone 6cs: KF96-6cs produced by Shin-Etsu Silicones

Formulation Example 9 (Deodorant Gel)

A deodorant gel was prepared from the composition comprising the below shown (a) to (f) and found to have rank 5 for feeling in use when dry and rank 4 for feeling in use when sweating. The deodorazing effect was confirmed.

| | | |
|---|---|---|
| a) | copolymer of acrylic acid and alkyl methacrylate, Carbopol C981 (tradename of Goodrich Corporation) | 0.3 weight % |
| b) | Triclosan | 0.1 weight % |
| c) | silicone powder, KMP599 (tradename of Shietsu Chemical Co., Ltd.) | 1.0 weight % |
| d) | the water-absorbing polymer of Example 1 | 2.0 weight % |
| e) | ethanol | 3.0 weight % |
| f) | water | balance for 100 wt. % |

Formulation Example 10 (Deodorant Sheet)

A dispersion was prepared from the composition comprising the below shown (b) to (f) so as to have an impregnating rate to (a) of 270% and a solvent amount to (a) of 108 g/m² found to have rank 5 for feeling in use when dry and rank 5 for feeling in use when sweating. The deodorazing effect was confirmed.

| | | |
|---|---|---|
| a) | Pulp sheet having 40 g/cm² | 0.3 weight % |
| b) | the water-absorbing polymer of Example 1 | 2.0 weight % |
| c) | dimethycone 6cs | 5.0 weight % |
| d) | ethanol | 15.0 weight % |
| e) | ethyl p-oxybenzoate | 0.1 weight % |
| f) | water | balance for 100 wt. % |

Dimethycone6cs was KF96-6cs (tradename of Shinetsu Slicones).

The invention claimed is:

1. A silicone-modified water-absorbing polymer particle comprising:
   i) a water-absorbing polymer particle; and
   ii) a silicone compound having at least one amino group,
      wherein a surface of said particle is coated via chemical bonding to said silicone compound having at least one amino group and at least two or more silicon atoms,
      wherein said particle has an average particle size of from 1 to 50 μm.

2. The silicone-modified water-absorbing polymer particle of claim 1, wherein said water-absorbing polymer particle comprises a crosslinked (co)polymer of a hydrophilic vinyl monomer.

3. The silicone-modified water-absorbing polymer particle of claim 1, wherein said amino group capable of chemical bonding to the surface of said water-absorbing polymer bonds by covalent bonding, ionic bonding or both.

4. The silicone-modified water-absorbing polymer particle of claim 1, wherein said silicone compound is hydrophobic.

5. The silicone-modified water-absorbing polymer particle of claim 1, wherein said silicone compound having at least one amino group has a weight average molecular weight of the 1000 to 500,000.

6. The silicone-modified water-absorbing polymer particle of claim 1, wherein said water-absorbing polymer is comprised of a polymer having a crosslinked structure.

7. The silicone-modified water-absorbing polymer particle of claim 1, wherein said water-absorbing polymer is comprised of a polymer selected from the group consisting of starch, carrageenan, gelatin, agar, tragacanth gum, viscose, cellulose or crosslinked products thereof.

8. The silicone-modified water-absorbing polymer particle of claim 1, wherein said water-absorbing polymer is comprised of a polymer selected from the group consisting of crystalline cellulose, methyl cellulose, ethyl cellulose, hydroxyethyl cellulose carboxymethyl cellulose and a mixture thereof.

9. The silicone-modified water-absorbing polymer particle of claim 1, wherein said water-absorbing polymer is comprised of starch-(meth)acrylate graft copolymers.

10. The silicone-modified water-absorbing polymer particle of claim 1, wherein said water-absorbing polymer is comprised of a crosslinked product of a (co)polymer of a hydrophilic monomer.

11. The silicone-modified water-absorbing polymer particle of claim 1, wherein said water-absorbing polymer is comprised of monomers selected from the group consisting of (meth)acrylic acid, maleic acid, fumaric acid, crotonic acid, itaconic acid, 2-(meth)acryloyl ethane sulfonic acid, 2-(meth)acryloyl propane sulfonic acid, 2-(meth)acrylamide-2-methyl propane sulfonic acid, vinyl sulfonic acid, styrene sulfonic acid, (meth)acrylamide, N-substituted (meth)acrylamide, 2-hydroxyethyl (meth)acrylate, 2-hydroxypropyl (meth)acrylate, methoxypolyethylene glycol (meth)acrylate, polyethylene glycol(meth)acrylate, N-vinyl pyrrolidone and N-vinyl acetamide, amino-group containing monomers and a mixture thereof 12. The silicone-modified water-absorbing polymer particle of claim 1 obtained by polymerizing a hydrophilic vinyl monomer by reverse phase suspension polymerization in the presence of a silicone compound having at least one amino group.

13. A method for producing the silicone-modified water-absorbing polymer particle of claim 1 comprising polymerizing a hydrophilic vinyl monomer by reverse phase suspension polymerization in the presence of a silicone compound having at least one amino group,
   wherein a surface of said water-absorbing polymer particle has been coated via chemical bonding with said silicone compound having at least one amino group.

14. A method for producing the silicone-modified water-absorbing polymer particle of claim 1 comprising heating a water-absorbing polymer particle and a silicone compound having at least one amino group, in the presence of water,
   wherein a surface of said water-absorbing polymer particle has been coated via chemical bonding with said silicone compound having at least one amino group.

15. A cosmetic composition comprising a water-absorbing polymer particle comprising:
   i) a water-absorbing polymer particle; and
   ii) a silicone compound having at least one amino group,
      wherein a surface of said particle is coated via chemical bonding to said silicone compound having at least one amino group and at least two or more silicon atoms,
      wherein said particle has an average particle size of from 1 to 50 μm.

* * * * *